(12) United States Patent
Richardson

(10) Patent No.: US 9,365,424 B2
(45) Date of Patent: Jun. 14, 2016

(54) CHLORINE DIOXIDE GENERATOR USING REDOX RESIN AND ADSORBED CHLORITE SALT

(71) Applicant: University of Florida Research Foundation, Inc., Gainesville, FL (US)

(72) Inventor: David Ernest Richardson, Gainesville, FL (US)

(73) Assignee: UNIVERSITY OF FLORIDA RESEARCH FOUNDATION, INC., Gainesville, FL (US)

(*) Notice: Subject to any disclaimer, the term of this patent is extended or adjusted under 35 U.S.C. 154(b) by 0 days.

(21) Appl. No.: 14/772,182

(22) PCT Filed: Mar. 4, 2014

(86) PCT No.: PCT/US2014/020178
§ 371 (c)(1),
(2) Date: Sep. 2, 2015

(87) PCT Pub. No.: WO2014/138000
PCT Pub. Date: Sep. 12, 2014

(65) Prior Publication Data
US 2016/0002037 A1 Jan. 7, 2016

Related U.S. Application Data

(60) Provisional application No. 61/772,603, filed on Mar. 5, 2013.

(51) Int. Cl.
*B01J 20/00* (2006.01)
*C01B 11/02* (2006.01)
*A61L 2/18* (2006.01)
*A61L 9/014* (2006.01)
*A01N 59/00* (2006.01)

(52) U.S. Cl.
CPC ............... *C01B 11/024* (2013.01); *A01N 59/00* (2013.01); *A61L 2/18* (2013.01); *A61L 9/014* (2013.01); *A61L 2209/133* (2013.01)

(58) Field of Classification Search
CPC .......................................................... B01J 20/00
USPC ....................................................... 502/407
See application file for complete search history.

(56) References Cited

U.S. PATENT DOCUMENTS

| | | | |
|---|---|---|---|
| 3,684,437 A | 8/1972 | Callerame | |
| 5,567,405 A | 10/1996 | Klatte et al. | |
| 5,730,948 A | 3/1998 | Klatte et al. | |
| 5,853,689 A | 12/1998 | Klatte | |
| 7,087,208 B2 | 8/2006 | Sampson et al. | |
| 7,824,556 B2 | 11/2010 | Sampson et al. | |
| 7,964,138 B2 | 6/2011 | Richardson et al. | |
| 8,323,563 B2 | 12/2012 | Richardson et al. | |
| 2005/0224750 A1 | 10/2005 | Yang et al. | |
| 2011/0250123 A1 | 10/2011 | Sampson et al. | |

*Primary Examiner* — Edward Johnson
(74) *Attorney, Agent, or Firm* — Saliwanchik, Lloyd & Eisenschenk

(57) ABSTRACT

A chlorite salt-absorbent particle is prepared by absorbing a water soluble chlorite salt or a concentrated chlorite salt solution in an absorbent particle. The absorbent can be a silica gel particle or other particulate absorbent that can release the chlorite salt as an aqueous solution over time by simply contacting the chlorite salt-absorbent particle with water. The chlorine salt is extracted from the chlorite salt-absorbent particle over a period of minutes while being flushed with water. A chlorine dioxide generator in the form of a cartridge includes the chlorite salt-absorbent particles and an acid resin or a redox resin. Water can be introduced into an inlet of the cartridge and passes sequentially through the chlorite salt-absorbent particles and the acid resin or the redox resin with the discharge of a chlorine dioxide solution from the outlet of the cartridge.

10 Claims, 1 Drawing Sheet

CHLORINE DIOXIDE GENERATOR USING REDOX RESIN AND ADSORBED CHLORITE SALT

CROSS-REFERENCE TO RELATED APPLICATIONS

This application is the U.S. national stage application of International Patent Application No. PCT/US2014/020178, filed Mar. 4, 2014, which claims the benefit of U.S. Provisional Application Ser. No. 61/772,603, filed Mar. 5, 2013, the disclosures of which are hereby incorporated by reference in their entireties, including any figures, tables, or drawings.

BACKGROUND OF INVENTION

Chlorine dioxide ($ClO_2$) is a gaseous sterilizing agent used as a bactericide, viricide, and sporicide. Chlorine dioxide is also an effective microbicide in solution that can also destroy many chemical substances and toxins. Chlorine dioxide has excellent environmental qualities, as it does not produce large quantities of chlorinated hydrocarbon byproducts. Generally, the stability of $ClO_2$ solutions does not lend itself to long-term storage. For this reason, chlorine dioxide solutions are generated immediately before use.

Many processes, such as electrolysis and chemical mixing, are known for the production of $ClO_2$ in gas or solution forms suitable for large-scale use. Usually, sophisticated equipment and significant amounts of power are needed to produce $ClO_2$ by electrolysis of chlorite solutions. When prepared chemically, the reaction components must be maintained separately until mixing for the production of chlorine dioxide.

Chlorine dioxide solutions can be produced by treatment of chlorite salt solutions (e.g. $NaClO_2$) with a strong acid (for example, sulfuric acid) to produce acidic solutions that contain $ClO_2$. Ion exchange media can be used for the formation of chlorine dioxide; for example, U.S. Pat. No. 3,684,437 to Callerame discloses production of chlorine dioxide by ion exchange between a mixed bead cation-anion exchange resin and a chlorite of an alkali metal or an alkaline earth metal with a very slow flow rate. Similarly, U.S. Pat. Nos. 7,087,208 and 7,824,556, both to Sampson et al., disclose generation of chlorous acid from a chlorite salt precursor by passing an aqueous solution of the precursor through a cationic ion exchange resin in a hydrogen ion (acid) form and a catalytic material to accelerate the decomposition of chlorous acid to chlorine dioxide using gravity feed at a moderate rate.

More recently, U.S. Pat. Nos. 7,964,138 and 8,323,563 to Richardson et al. have disclosed chlorine dioxide generation with a generator that uses a chlorite bound ion exchange resin with an acid feed solution or an oxidant feed solution, such as, aqueous chlorine or bromine. Furthermore, U.S. Pat. Nos. 7,964,138 and 8,323,563 describe use of an oxidant bound ion exchange resin, for example, a $Br_3^-$ bound resin, and a chlorite feed solution. The generator based on these patents can be portable for the production of chlorine dioxide solution on demand at a reasonably rapid controlled rate.

Although the method of Richardson et al. is useful for commercial and even portable emergency production of chlorine dioxide, the containment and storage of a relatively large amount of an isolated aqueous solution as the feed solution is required. Therefore, a method of retaining both complementary reagents in a bound state, such that any available water as the liquid feed, rather than a specific precursor-containing solution, would be desirable to reduce the complexity and volume of a chlorine dioxide generator. A first bound reagent would be situated upstream of its complementary second bound reagent, and would need to be in a state where the first bound reagent could be dissolved into an aqueous solution in a controlled manner. The total quantity of the first reagent must not be passed immediately from the system and the desired chlorine dioxide solution should be of a nearly constant concentration over a practical period of discharge.

BRIEF SUMMARY

An embodiment of the invention is directed to a chlorite salt-absorbing particle where a solid particulate absorbent is combined with a chlorite salt for releasing the chlorite salt when washed with water over a period of time with a salt delivery at a sustained rate and concentration that is practical for production of chlorine dioxide solutions. The rate of delivery may be selected for use in immediate decontamination or other use or, alternatively, for safe and efficient production of a batch solution of chlorine dioxide. In an embodiment of the invention, an alkali metal chlorite salt is combined with silica gel particles to form a chlorite salt-absorbent particle. Contacting with water in the form of a pure liquid or a solution of spectator solutes that are not present for reaction or exchange with the chlorite salt-absorbent results in an aqueous chlorite salt solution.

An embodiment of the invention is directed to a device for the preparation of a chlorine dioxide solution. The device consists of a cartridge that contains the chlorite salt-absorbent particle and a redox resin that allows production of chlorine dioxide solution introducing pure water. Alternatively, an acid resin can be used instead of a redox resin. The water can be included with the device or water can be provided from that available at any location. The device may consist of a single multi-part cartridge for convenience or it may consist of linked containers containing the required adsorbents containing the separated reagents.

DETAILED DISCLOSURE

Figure 1:
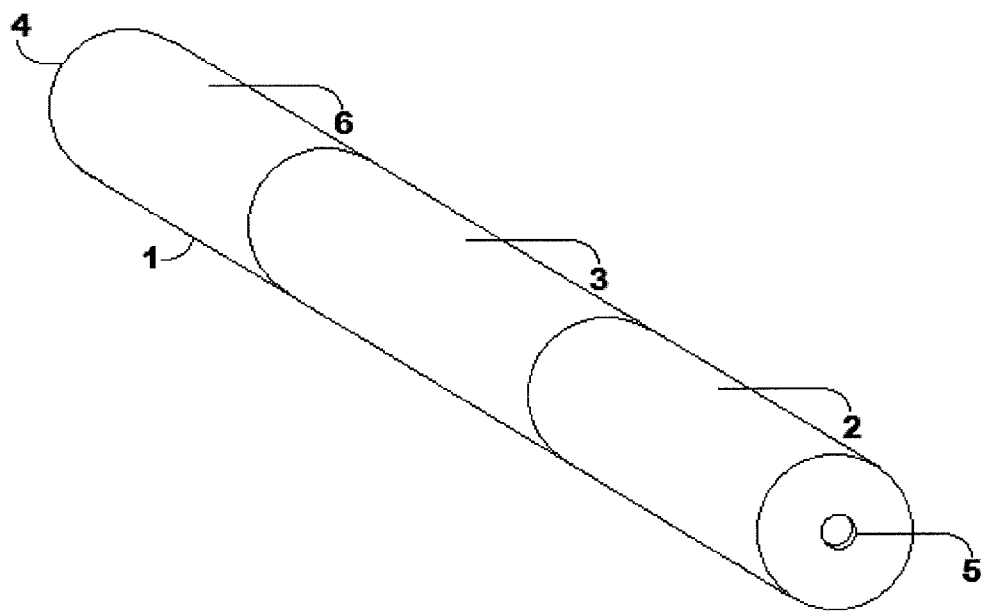
FIG. 1 shows a sketch of a simple one container cartridge chlorine dioxide generator, according to an embodiment of the invention.

An embodiment of the invention is directed to a solid particle with an absorbed chlorite salt, a chlorite salt-absorbent particle that allows the washing of a chlorite salt from the absorbent over a period of sufficient length to allow decontamination or treatment of an area or a quantity of material for practical use. For example, the chlorite salt-absorbent particle can release the chlorite salt over a period of about one to about 30 minutes or more as water or another appropriate solvent flows through the device. The release is not a rapid release such as that which occurs when sodium chlorite or another highly soluble salt is brought in contact with water. In an exemplary embodiment of the invention, porous dry silica gel beads are contacted with a concentrated sodium chlorite solution where the sodium chlorite solution is absorbed into the micro-channels within the silica gel. The silica gel and the chlorite salt-absorbent particle formed therefrom can be in the form of free flowing beads, or any other form that readily permits the flow of water through a bed of the chlorite salt-absorbent particle. A portion of the water can be removed from the beads as desired. In this manner, a relatively high concentration of sodium chlorite, or any other soluble metal chlorite, can be loaded to a high level in a relatively free flowing particulate solid. This particulate solid can have dimensions from about 10 micrometers to about 3 millimeters or more in cross-section. The particles can be regular, for example, spheres, or irregular, for example, a ground powder, in appearance. The desired size is that practical for the environment where the solid chlorite salt-absorbent is to be used and is selected to provide appropriate flow rate and rate of chlorite release.

In embodiments of the invention, solid chlorite salt-absorbent particles, for example, small beads, can be combined in a cartridge with a resin bound oxidant (redox resin) or a resin bound acid (acid resin). For example, a strong acid cation exchange resin can be combined with the chlorite salt-absorbent particles in a cartridge housing. For example, as desired, the resin can be a solid ion exchange medium in the acid (H+) form of an ion exchange resin, such as Dowex™ cationic exchange resins. In another embodiment of the invention, an anion exchange resin in a $Br_3^-$ or $Cl_3^-$ form can be used with the chlorite salt-absorbent particles. For example, a $Br_3^-$ can be bound to an ion exchange resin by passing a bromine water solution through an anionic exchange resin with bound $Br^-$ ions. For example, an Amberlite™ anion exchange or resin in the $Cl^-$ form is washed with dilute hydrochloric acid and subsequently with a NaBr solution to achieve a $Br^-$ bound resin. After washing free $Br^-$ from the resin with water, saturated aqueous bromine can be washed through the $Br^-$ bound resin and subsequently washed with water to form a $Br_3^-$ bound resin. In another embodiment of the invention, a $Cl_3^-$ bound resin can be formed in the manner disclosed in U.S. Provisional Patent Application No. 61/682,368, filed on Aug. 13, 2012, which is incorporated herein by reference and attached herewith. The chlorite salt-absorbent is situated in a portion of the cartridge between an inlet for water introduction and the resin bound oxidant or resin bound acid near an outlet for a chlorine dioxide solution. Alternately, the two reagent-containing particulate solids can be separated into two containers linked to allow flow of water or another solvent through the system in the appropriate sequence.

In addition to silica gel particles, other materials that can form a chlorite salt-absorbent include any porous material where a salt solution can be infused within the pores, and retained where the surface of the particles can be sufficiently dry for inclusion in the cartridge but where the pores retain the salt as a solid film or a concentrated solution until washed from the particles upon contacting with water. The pores can have effective diameters that are in excess of about 4 nm to about 100 microns. In an embodiment of the invention, the porous material can be a porous polymer, such as an unfunctionalized macroreticular resin, for example, a polystyrene resin or an acrylate resin, or a functionalized macroreticular resin, for example, a cation exchange resin where the cation is an alkali metal, where the release of the chlorite is controlled primarily by the rate of diffusion of water and chlorite salt through the pores of the resin particles. In another embodiment of the invention, the chlorite salt-absorbent particles can be hydrogel particles, for example, a crosslinked polyethylene oxide, polyvinyl alcohol, poly(sodium acrylate), or other hydrogel. The hydrogel may be porous or non-porous, where the rate of water diffusion through the gel exceeds the rate of diffusion of the chlorite salt, and the dimensions of the gel particles are appropriate for sustained delivery of the chlorite salt. In another embodiment of the invention, the adsorbent can be a zeolite of appropriate form to absorb a salt solution, such as a molecular sieve. The absorbent can be of any material that is not oxidized by a concentrated chlorite salt solution and where no agent in addition to the water is required for desorption of the chlorite salt from the absorbent.

The cartridge can be a stand-alone device or a device for incorporation into a larger device designed to accept a cartridge. The cartridge permits deliveries of a controlled concentration of chlorine dioxide effluent upon introduction of water or an aqueous solution to the inlet of the cartridge. The device does not require a mixer or flow controller. In its simplest form, the device can produce chlorine dioxide solution by a gravity flow of water through the cartridge to produce nearly an equal volume of chlorine dioxide solution to that of the water introduced, where the difference is only the minimal amount required to wet the resins and absorbent particles in the cartridge. Alternately, the water flow can be a forced flow due to the imposition of a pressure differential. For example, water flow can be that due to the water pressure provided by a typical municipal water utility system. A pump, a syringe, an aspirator, or any other means of providing a pressure differential can be included to induce a water flow through the cartridge. The cartridges can be, but are not necessarily, portable to allow chlorine dioxide generation as needed at a site where decontamination or treatment of environmental surfaces, water, equipment, or biological surfaces is needed. For example, a cartridge can be used by deployed military personnel or other individuals that are involve in remote areas where they may be exposed to bacteria, viruses, fungi, other pathogens, or chemicals that can be rendered harmless upon oxidation by chlorine dioxide. In many applications, for example, the preformed assembly requires only the addition of water from local sources to produce the desired chlorine dioxide solution, thus reducing the mass and volume of the device that is transported or stored for future use. A further advantage of the cartridge device is that the chlorine dioxide solution produced can decontaminate the water used to prepare the chlorine dioxide solution, and, therefore, the water used need not be potable or decontaminated prior to use.

In an embodiment of the invention, the cartridge chlorine dioxide generator, as shown in FIG. 1, comprises: a housing 1; a redox resin 2, for example, a $Cl_3^-$ resin; chlorite salt-absorbent particles 3, for example, silica gel with absorbed concentrated sodium chlorite solution; a water inlet 4; and a chlorine dioxide solution outlet 5. The housing can be any material that is resistant to a chlorine dioxide solution or a combination of materials where the portion of the housing in contact with chlorine dioxide solution is resistant to degradation by chlorine dioxide. The dimensions of the portions of the cartridge that contains the redox resin and the chlorite salt-absorbent, the diameter of the inlet and outlet, and the length, diameter, and shape of the cartridge can vary significantly and is not necessarily a cylinder, as shown in FIG. 1. The proportion of redox resin to the chlorite salt-absorbent can vary to achieve stoichiometrically equivalent amounts of the bound reagents or permit an excess of one reagent or the other as desired, for example, having an excess of the redox resin. The cartridge may include removable caps to seal the inlet and outlet for dry storage of the cartridge before use. The cartridge may include valves or break-seals at the inlet, outlet, and/or between the chlorite salt-absorbent and redox resin. The cartridge may include a void volume 6 between the inlet and the chlorite salt-absorbent to accept an appropriate volume of water to be delivered to the chlorite salt-absorbent and redox resin. The cartridge may include a means for connecting a water supply, for example, a hose barb, a joint, or screw threads at the inlet end of the cartridge. The outlet from the cartridge may include a means for connection, or may include a nozzle for spraying of the chlorine dioxide solution.

Figure 2:
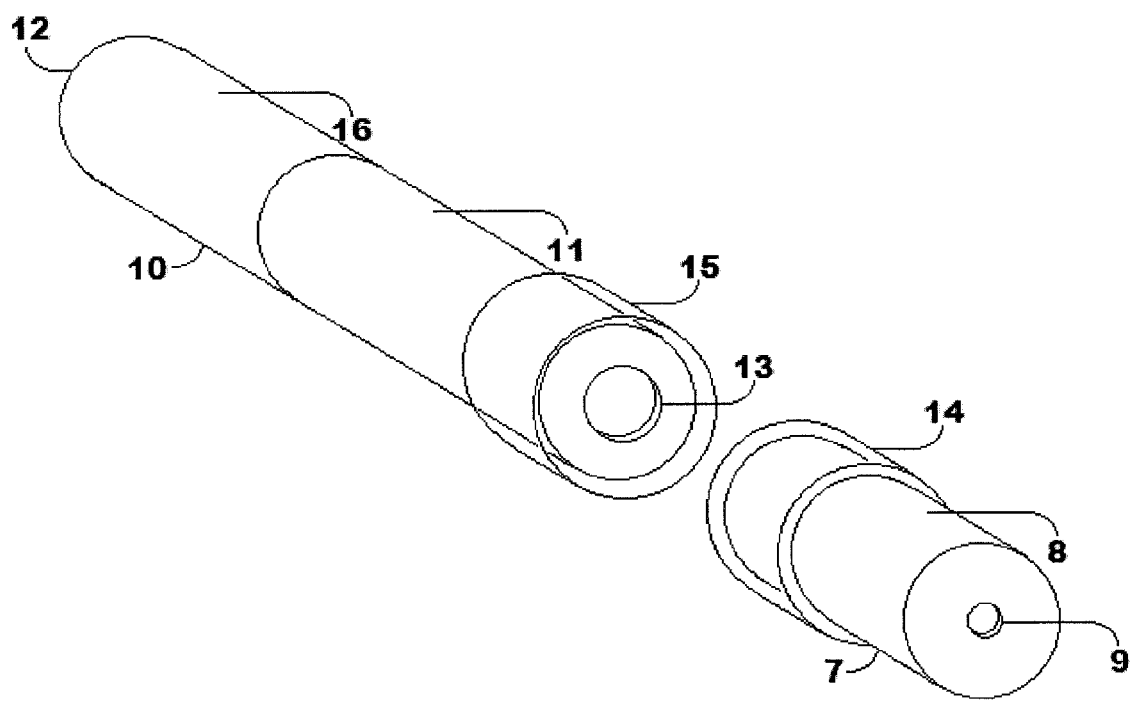
FIG. 2 shows a sketch of a device separated into two containers that can be linked, according to an embodiment of the invention.

In another embodiment of the convention, the two-container chlorine dioxide generator, as shown in FIG. 2, comprises: a first container with a housing 7 containing a redox resin 8, such as a $Cl_3^-$ resin and a chlorine dioxide solution outlet 9; and a second container with a housing 10, containing chlorite salt-absorbent particles 11, for example, a $Cl_3^-$ resin; chlorite salt-absorbent particles, a water inlet 12, and a chlorite salt solution outlet 13. The containers and plumbing can be any material that is resistant to a chlorine dioxide solution or a combination of materials where the portion of the device in contact with chlorine dioxide solution is resistant to degradation by chlorine dioxide. The dimensions of the portions of the containers that contains the redox resin and the chlorite salt-absorbent, the diameter of the inlet and outlet, and the length, diameter, and shape of the cartridge can vary significantly, not of equal volume as shown in FIG. 2. The proportion of redox resin to the chlorite salt-absorbent can vary to achieve stoichiometrically equivalent amounts of the bound reagents or permit an excess of one reagent or the other as desired, for example, having an excess of the redox resin. The device may include removable caps 14 and 15, as shown in FIG. 2, on the ends to connect the first and second containers and may include caps to seal the inlet and outlet for dry storage of the cartridge before use. The cartridge may include valves or other control device between the chlorite salt-absorbent and redox resin. The device may include a void volume 16 of appropriate volume prior to the chlorite salt-absorbent of the second container to accept a portion or all of the water to be delivered to the chlorite salt-absorbent and redox resin. Alternatively, the void volume 16 may be in a third container separated from the second container and may be connected by any means to the second container when desired. The device may include a means for connecting a water supply, for example, a hose barb, a joint, or screw threads at the inlet end of the cartridge. The outlet from the cartridge may include a means for connection and flow control, or may include a nozzle for spraying or dispensing of the chlorine dioxide solution. The first, second, and third containers may be connected directly to each other or by a tube or other conduit, for example, a tube can be connected to the chlorite salt solution outlet of the first container and the inlet to the second container. Connection can be by any means, such as matching male and female threading on the housings of the first and second containers.

All patents and provisional applications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A chlorite salt-absorbent particle, comprising a chlorite salt or mixture of salts in an absorbent particle, wherein the chlorite salt is bound physically in the chlorite salt-absorbent particle and the chlorite salt-absorbent particle permits the release of the chlorite salt to contacting water over a sustained period in excess of a minute.

2. The chlorite salt-absorbent particle of claim 1, wherein the chlorite salt is an alkali metal chlorite.

3. The chlorite salt-absorbent particle of claim 1, wherein the absorbent particle is porous.

4. The chlorite salt-absorbent particle of claim 3, wherein the absorbent particle is a silica gel particle.

5. The chlorite salt-absorbent particle of claim 1, wherein the chlorite salt-absorbent particle has a cross-section of 10 nm to 3 mm.

6. A cartridge chlorine dioxide generator, comprising a housing, a plurality of chlorite salt-absorbent particles according to claim 1, and an acid resin or a redox resin, wherein the chlorite salt-absorbent particles and the acid resin or the redox resin are situated within separate portions of the housing and wherein the cartridge comprises one or more containers.

7. The cartridge chlorine dioxide generator of claim 6, wherein the acid resin is a cationic exchange resin in a hydrogen form.

8. The cartridge chlorine dioxide generator of claim 6, wherein the redox resin is an anionic exchange resin in a $Cl_3^-$ or $Br_3^-$ form.

9. A method of generating chlorine dioxide comprising:
    providing water;
    providing a plurality of chlorite salt-absorbent particles according to claim 1;
    providing an acid resin or a redox resin;
    directing a flow of the water through the chlorite salt-absorbent particles and subsequently through the acid resin or the redox resin; and
    discharging a chlorine dioxide comprising solution.

10. The method of claim 9, wherein the chlorite salt-absorbent particles and the acid resin or the redox resin reside within a cartridge chlorine dioxide generator according to claim 6.

* * * * *